United States Patent [19]

Fisher et al.

[11] Patent Number: 5,576,313
[45] Date of Patent: Nov. 19, 1996

[54] INHIBITORS OF FARNESYL-PROTEIN TRANSFERASE

[75] Inventors: Thorsten E. Fisher, Hatfield; John S. Wai, Harleysville; J. Christopher Culberson, Hatfield, all of Pa.; Walfred S. Saari, St. George, Me.

[73] Assignee: Merck & Co., Inc., Rahway, N.J.

[21] Appl. No.: 298,478

[22] Filed: Aug. 29, 1994

[51] Int. Cl.$^6$ .................... A61K 31/435; A61K 31/44; A61K 31/54; A61K 31/545; C07D 211/06; C07D 401/12; C07D 413/14; C07D 417/14

[52] U.S. Cl. ............... 514/211; 514/217; 514/222.2; 514/227.8; 514/228.8; 514/31.5; 514/241; 514/247; 514/256; 514/290; 514/307; 514/311; 514/314; 514/315; 514/316; 514/317; 514/318; 514/318; 514/320; 514/321; 514/322; 514/323; 514/324; 514/326; 514/330; 540/519; 540/524; 544/14; 544/55; 544/60; 544/111; 544/224; 544/233; 544/238; 544/245; 544/338; 544/359; 546/79; 546/139; 546/148; 546/149; 546/152; 546/187; 546/189; 546/193; 546/195; 546/196; 546/197; 546/198; 546/200; 546/201; 546/205; 546/207; 546/208; 546/209; 546/210; 546/212; 546/214; 546/226

[58] Field of Search ............... 514/315, 330, 514/316, 317, 318, 319, 320, 321, 322, 323, 324, 326, 211, 217, 222.2, 227.8, 228.8, 231.5, 241, 247, 256, 290, 307, 311, 314; 546/226, 187, 189, 193, 195, 196, 197, 198, 200, 201, 205, 207, 208, 209, 210, 212, 214, 79, 137, 148, 149, 152; 540/519, 524; 544/14, 55, 60, 111, 224, 233, 238, 245, 338, 359

[56] References Cited

U.S. PATENT DOCUMENTS

| | | | |
|---|---|---|---|
| 5,043,268 | 8/1991 | Stock | 514/307 |
| 5,141,851 | 8/1992 | Brown et al. | 435/15 |
| 5,238,922 | 8/1993 | Graham et al. | 514/357 |
| 5,326,773 | 7/1994 | De Solms et al. | 514/18 |
| 5,340,828 | 8/1994 | Graham et al. | 514/357 |
| 5,352,705 | 10/1994 | Deana et al. | 514/630 |
| 5,362,906 | 11/1994 | Anthony et al. | 514/357 |

FOREIGN PATENT DOCUMENTS

| | | |
|---|---|---|
| 0456180A1 | 11/1991 | European Pat. Off. . |
| 0618221A2 | 10/1994 | European Pat. Off. . |
| WO91/16340 | 10/1991 | WIPO . |
| WO94/26273 | 11/1994 | WIPO . |
| WO94/28720 | 12/1994 | WIPO . |

OTHER PUBLICATIONS

Okolicany et al, Chemical Abstracts, vol. 116 No. 35046, 1991 "Effects of small C-ANF receptor ligands on plasma levels".

Gibbs, J. B. et al., "Selective Inhibition of Farnesyl-Protein Transferase Blocks Ras Processing in Vivo", The Journal of Biological Chemistry, vol. 268, No. 11, pp. 7617-7620 (1993).

Goldstein, J. L. et al., "Nonfarnesylated Tetrapeptide Inhibitors of Protein Farnesyltranferase", The Journal of Biological Chemistry, vol. 266, No. 24 pp. 15575-15578 (1991).

James, G. L. et al., "Benzodiazepine Peptidomimetic BZA-5B Interrupts the MAP Kinase Activation Pathway in H-Ras-transformed Rat-1 Cells, but Not in Untransformed Cells", The Journal of Biological Chemistry, vol. 369, No. 44, pp. 27705-27714 (1994).

James, G. L. et al., "Benzodiazepine Peptidomimetics: Potent Inhibitors of Ras Farnesylation in Animal Cells", Science, vol. 260, pp. 1937-1942 (1993).

Kohl, N. E. et al., "Selective Inhibition of ras-Dependent Transformation by a Farnesyltransferase Inhibitor", Science, vol. 260, pp. 1934-1937 (1993).

Kohl, N. E. et al., "Protein farnesyltransferase inhibitors block the growth of ras-dependent tumors in nude mice", Proc. Natl. Acad. Sci. USA, Med. Sciences, vol. 91, pp. 9141-9145 (1994).

Pompliano, D. L., "Steady-State Kinetic Mechanism of Ras Farnesyl:Protein Transferase", Biochemistry, vol. 31, pp. 3800-3807 (1992).

Primary Examiner—C. Warren Ivy
Assistant Examiner—Raymond Covington
Attorney, Agent, or Firm—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and treatment of cancer.

11 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989)). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.*

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et. al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosol localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of Ras, and other cellular proteins, with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et al., ibid; Reiss et al., *PNAS*, 88:732–736 (1991)). It was, however, disclosed that tetrapeptides which further contained a cyclic amino acid residue, such as proline, had greatly reduced inhibitory activity when compared to tetrapeptides not containing a cyclic amino acid (Reiss et al., (1991)). Tetrapeptide inhibitors may inhibit while serving as alternate substrates for the Ras farnesyltransferase enzyme, or may be purely competitive inhibitors (U.S. Pat. No. 5,141,851, University of Texas).

Recently, it has been demonstrated that certain inhibitors of farnesyl-protein transferase selectively block the processing of Ras oncoprotein intracellularly (N. E. Kohl et al., *Science*, 260:1934–1937 (1993) and G. L. James et al., *Science*, 260:1937–1942 (1993)).

Among the inhibitors of farnesyl protein transferase that have been described in the art are benzodiazepine derivatives that mimic the CAAX motif of a prenylated protein (James, et al., *Science*, 1993, 260, 1937–1942). These compounds are potent inhibitors of FPTase. However, the compounds described by James, et al., are carboxylic acids which have relatively poor activity as inhibitors of farnesylation in intact cells. To render such compounds useful for inhibition of the transformed phenotype of a cancer cell, esterification of the C-terminal carboxylate is required. Such a prodrug strategy significantly complicates the clinical application of an FPTase inhibitor by adding additional variables to its pharmokinetic and pharmodynamic behavior.

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

It is also the object of the invention to provide a FPTase inhibitor which includes substituted piperidine analogs which inhibit farnesyl-protein transferase and the farnesylation of the oncogene protein Ras p21, and chemotherapeutic compositions containing the compounds of this invention.

SUMMARY OF THE INVENTION

The present invention includes substituted piperidine analogs which inhibit farnesyl-protein transferase and the farnesylation of the oncogene protein Ras p21. This invention also includes chemotherapeutic compositions containing the compounds of this invention, methods of inhibiting farnesyl-protein transferase and methods for treating cancer.

The compounds of this invention are illustrated by the Formula I:

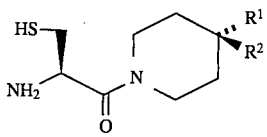

DETAILED DESCRIPTION OF THE INVENTION

The compounds of this invention are useful in the inhibition of farnesyl-protein transferase and the farnesylation of the oncogene protein Ras p21. In an embodiment of this invention, the inhibitors of farnesyl-protein transferase are illustrated by Formula I:

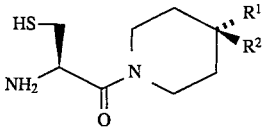

wherein:
$R^1$ is selected from:
  a) COR,
  b) $CO_2R$,
  c) CONHR,
  d) OH,
  e) OCOR,
  f) CN,
  g) $CH_2OR$,
  h) NHCOR,
  i) $NHSO_2R$, or
  j) $COR^5$;
R is selected from:
  a) $C_{1-4}$ alkyl, unsubstituted or substituted with:
    i) $C_{1-4}$ alkoxy,
    ii) $NR^3R^4$,
    iii) $C_{3-6}$ cycloalkyl,
    iv) aryl or heterocycle; or
  b) aryl or heterocycle;
$R^2$ is selected from: aryl, aralkyl, heterocycle, or heteroaralkyl, unsubstituted or substituted with one or more of:
  a) $C_{1-4}$ alkyl, unsubstituted or substituted with:
    i) $C_{1-4}$ alkoxy,
    ii) $NR^3R^4$,
    iii) $C_{3-6}$ cycloalkyl, or
    iv) aryl or heterocycle;
  b) aryl or heterocycle,
  c) halogen,
  d) $OR^3$,
  e) $NR^3R^4$,
  f) CN,
  g) $NO_2$, or
  h) $CF_3$;
$R^3$ and $R^4$ are independently selected from: H, $C_{1-4}$ alkyl, $C_{3-6}$ cycloalkyl, heterocycle, aryl, aroyl, heteroaryl, arylsulfonyl, heteroarylsulfonyl, unsubstituted or substituted with one or more of:
  a) $C_{1-4}$ alkoxy,
  b) aryl or heterocycle,
  c) halogen, or
  d) HO, wherein
or $R^3$ and $R^4$ may be joined in a ring;
$R^5$ is selected from:
  a) a naturally occurring amino acid, or
  b) an oxidized form of a naturally occurring amino acid which is:
    i) methionine sulfoxide, or
    ii) methionine sulfone;
or the pharmaceutically acceptable salt thereof.

The preferred compounds of this invention are:
L-Cysteinyl-4-(2-methylbenzyl)isonipecotyl-L-methionine;
L-Cysteinyl-4-benzyl isonipecotic acid methyl ester;
L-Cysteinyl-4-(2-methylbenzyl)isonipecotyl N-methyl amide;
L-Cysteinyl-4-(2-methylbenzyl)isonipecotyl N-(2-pyridylmethyl) amide;
L-Cysteinyl-4-(2-methylbenzyl)isonipecotyl N-benzyl amide;
L-Cysteinyl-4-(2-methylbenzyl)isonipecotic acid methyl ester;
L-Cysteinyl-4-(2-chlorobenzyl)isonipecotic acid methyl ester;
L-Cysteinyl-4-(2,3-dichlorobenzyl)isonipecotic acid methyl ester;
L-Cysteinyl-4-(2,4-dichlorobenzyl)isonipecotic acid methyl ester;
L-Cysteinyl-4-(2,6-dichlorobenzyl)isonipecotic acid methyl ester;
L-Cysteinyl-4-(3-(2-methyl)pyridylmethyl)isonipecotic acid methyl ester;
L-Cysteinyl-4-(1-naphthyl)methyl isonipecotic acid methyl ester;
L-Cysteinyl-4-(1-naphthyl)methyl isonipecotic acid ethyl ester;
L-Cysteinyl-4-(1-naphthyl)methyl isonipecotic acid benzyl ester;
L-Cysteinyl-4-(2-methylbenzyl)isonipecotic acid 2-pyridylmethyl ester;
L-Cysteinyl-4-(2-methylbenzyl)isonipecotic acid 3-pyridylmethyl ester;
L-Cysteinyl-4-(2-methylbenzyl)isonipecotic acid 4-pyridylmethyl ester;
L-Cysteinyl-4-benzyl-4-piperidinol;
L-Cysteinyl-4-acetoxy-4-benzylpiperidine;
L-Cysteinyl-4-cyano-4-phenylpiperidine;
L-Cysteinyl-4-acetyl-4-phenylpiperidine;
L-Cysteinyl-4-methoxymethyl-4-(2-methylbenzyl)piperidine;
L-Cysteinyl-4-acetamido-4-(2-methylbenzyl)piperidine;
L-Cysteinyl-4-methylsulfonamido-4-(2-methylbenzyl)piperidine;
or the pharmaceutically acceptable salts thereof.

The more preferred compounds of this invention are:

L-Cysteinyl-4-(2-methylbenzyl)isonipecotyl N-methyl amide;

L-Cysteinyl-4-(2-methylbenzyl)isonipecotyl N-(2-pyridylmethyl) amide;

L-Cysteinyl-4-(2-methylbenzyl)isonipecotyl N-benzyl amide;

L-Cysteinyl-4-(2-methylbenzyl)isonipecotic acid methyl ester;

L-Cysteinyl-4-(2-chlorobenzyl)isonipecotic acid methyl ester;

L-Cysteinyl-4-(2,3-dichlorobenzyl)isonipecotic acid methyl ester;

L-Cysteinyl-4-(2,4-dichlorobenzyl)isonipecotic acid methyl ester;

L-Cysteinyl-4-(2,6-dichlorobenzyl)isonipecotic acid methyl ester;

L-Cysteinyl-4-(3-(2-methyl)pyridylmethyl)isonipecotic acid methyl ester;

L-Cysteinyl-4-(1-naphthyl)methyl isonipecotic acid methyl ester;

L-Cysteinyl-4-(1-naphthyl)methyl isonipecotic acid ethyl ester;

L-Cysteinyl-4-(1-naphthyl)methyl isonipecotic acid benzyl ester;

L-Cysteinyl-4-(2-methylbenzyl) isonipecotic acid 2-pyridylmethyl ester;

L-Cysteinyl-4-(2-methylbenzyl) isonipecotic acid 3-pyridylmethyl ester;

L-Cysteinyl-4-(2-methylbenzyl) isonipecotic acid 4-pyridylmethyl ester;

L-Cysteinyl-4-benzyl-4-piperidinol;

L-Cysteinyl-4-methoxymethyl-4-(2-methylbenzyl)piperidine;

or the pharmaceutically acceptable salts thereof.

The most preferred compounds of this invention are:

L-Cysteinyl-4-(2,3-dichlorobenzyl)isonipecotic acid methyl ester;

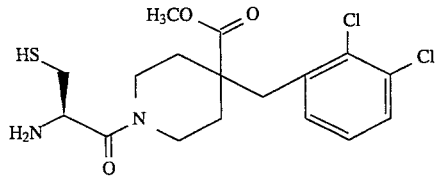

L-Cysteinyl-4-(2,4-dichlorobenzyl)isonipecotic acid methyl ester;

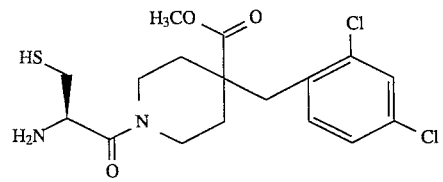

or the pharmaceutically acceptable salts thereof.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic.

Examples of such aryl elements include phenyl, naphthyl, tetrahydronaphthyl, indanyl, biphenyl, phenanthryl, anthryl or acenaphthyl.

The term "aralkyl" represents a branched or straight-chain saturated aliphatic hydocarbon groups having 1 to 4 carbon atoms, attached to any stable monocyclic, bicyclic or tricyclic carbon ring of up to 7 members in each ring, wherein at least one ring is aromatic.

The term heterocycle or heterocyclic, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and $S(O)_m$ (wherein m=0, 1 or 2), and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

The term "heteroaralkyl" is intended to mean a branched or straight-chain saturated aliphatic hydocarbon groups having 1 to 4 carbon atoms, attached to a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S(O)m (wherein m=0, 1 or 2), and including any bicyclic group in which any of the above-defined heterocyclic rings is fused to a benzene ring. The heterocyclic ring may be attached at any heteroatom or carbon atom which results in the creation of a stable structure.

In the present invention, the term "naturally occurring amino acids" represents both the D and L enantiomer separately and the racemic mixture of the following amino acids, which may be identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |

| | | |
|---|---|---|
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When $R^3$ and $R^4$ are joined, the cyclic amine substituent formed is a nitrogen containing ring, consisting of 4 to 6 members, optionally substituted with one of the following: O, S, or N. Examples of such cyclic amines include, but are not limited to: piperidine, piperazine, morpholine, azetidine, pyrolidine, and thiazolidine.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized by methods well known in the pharmaceutical arts, and the additional methods described below.

Abbreviations used in the description of the chemistry and in the Examples that follow are:

| | |
|---|---|
| Ac₂O | Acetic anhydride; |
| Boc | t-Butoxycarbonyl; |
| BOP | Bis(2-oxo-3-oxazolidinyl)phosphonic chloride; |
| CBz | Benzyloxycarbonyl; |
| DMAP | 4-Dimethylaminopyridine; |
| DMF | Dimethylformamide; |
| DPPA | Diphenylphosphoryl azide; |
| EDC | 1-(3-Dimethylaminopropyl)-3-ethyl-carbodiimide hydrochloride; |
| HOBT | 1-Hydroxybenzotriazole hydrate; |
| Et₃N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| KHMDS | Potassium bis(trimethylsilyl)amide; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran; |
| Tr | Trityl, triphenylmethyl. |

Synopsis of Reaction Schemes 1–8:

The compounds of this invention are prepared as illustrated by Reaction Schemes 1–8, in addition to other standard manipulations such as ester hydrolysis, cleavage of protecting groups, etc., as may be known in the literature or exemplified in the experimental procedures.

Specifically, Scheme 1 depicts the synthesis of the claimed amide analogs. The readily available N-Boc benzyl isonipecotate is alkylated by successive treatment with an amide base, such as lithium or sodium bis(trimethylsilyl)amide, or lithium diisopropylamide, followed by treatment with a 2-methyl benzyl halide. Hydrogenolysis of the benzyl ester, over a palladium on charcoal catalyst, furnishes the free carboxylic acid which is subsequently transformed into the amide by treatment with an amine or amine salt and an appropriate coupling reagent such as EDC. Boc deprotection of the piperidine nitrogen with anhydrous HCl provides the corresponding HCl salt which is coupled with the commercially available protected L-cysteine. Simultaneous amine and thiol deprotection with trifluoroacetic acid and triethylsilane, affords the claimed amide compounds.

The claimed ester analogs are prepared as illustrated in Scheme 2 by alkylating the readily available N-Boc isonipecotic acid esters with the appropriate benzyl halide in a manner similar to that described in Scheme 1. Subsequent coupling with the L-cysteine and simultaneous deprotection, also previously described, affords the ester analogs.

Scheme 3 depicts the preparation of the claimed pyridylmethyl esters which are achieved in a different sequence than those esters indicated in Scheme 2. In this sequence the N-Boc-4-(2-methylbenzyl)isonipecotic acid is converted to the pyridylmethyl ester with the corresponding pyridylmethyl carbinol and a coupling reagent such as EDC in combination with a catalytic amount of an activator such as DMAP. Subsequent cysteine coupling and deprotection as previously illustrated provides the pyridylmethyl ester analogs.

The 4-methoxymethylpiperidine analog is prepared via the route in Scheme 4. The benzyl ester of N-Boc 4-(2-methylbenzyl) isonipecotic acid is reduced with lithium aluminum hydride to the alcohol and then alkylated by treating the sodium salt with methyl iodide. The resulting methoxymethylpiperidine is deprotected, coupled with the L-cysteine and deprotected as previously described to afford the indicated methoxymethylpiperidine analog.

Scheme 5 shows the simple transformation of commercially available 4-cyano and 4-acetyl 4-phenyl piperidines to their products through previously described L-cysteine coupling and deprotection.

The hydroxypiperidine compound and its acetyl derivative are prepared as indicated in Scheme 6. Commercially available N-benzyl 4-piperidinone is treated with benzyl magnesium chloride to afford the benzyl alcohol. This compound is deprotected by hydrogenolysis over 10% palladium on charcoal catalyst to the free piperidine compound and then coupled to the protected L-cysteine in the previously indicated manner. The hydroxy compound is furnished by cysteine deprotection and its acetyl derivative by acetylation of the alcohol with acetic anhydride and a catalytic amount of DMAP followed by cysteine deprotection.

The synthesis of the claimed acetamido analog is depicted in Scheme 7. The protected 4-(2-methylbenzyl)isonipecotic acid undergoes a Curtius rearrangement by treatment with diphenylphosphoryl azide and triethylamine to afford the 4-aminopiperidine which is acetylated with acetic anhydride and then deprotected with anhydrous HCl. L-cysteine coupling and deprotection affords the indicated compound.

Preparation of the 4-methylsulfonylamido compound is shown in Scheme 8. The 4-amino-4-(2-methylbenzyl)piperidine is sulfonated with methane sulfonyl chloride, deprotected, coupled with the L-cysteine and a final deprotection affords the claimed compound.

5,576,313
REACTION SCHEME 1
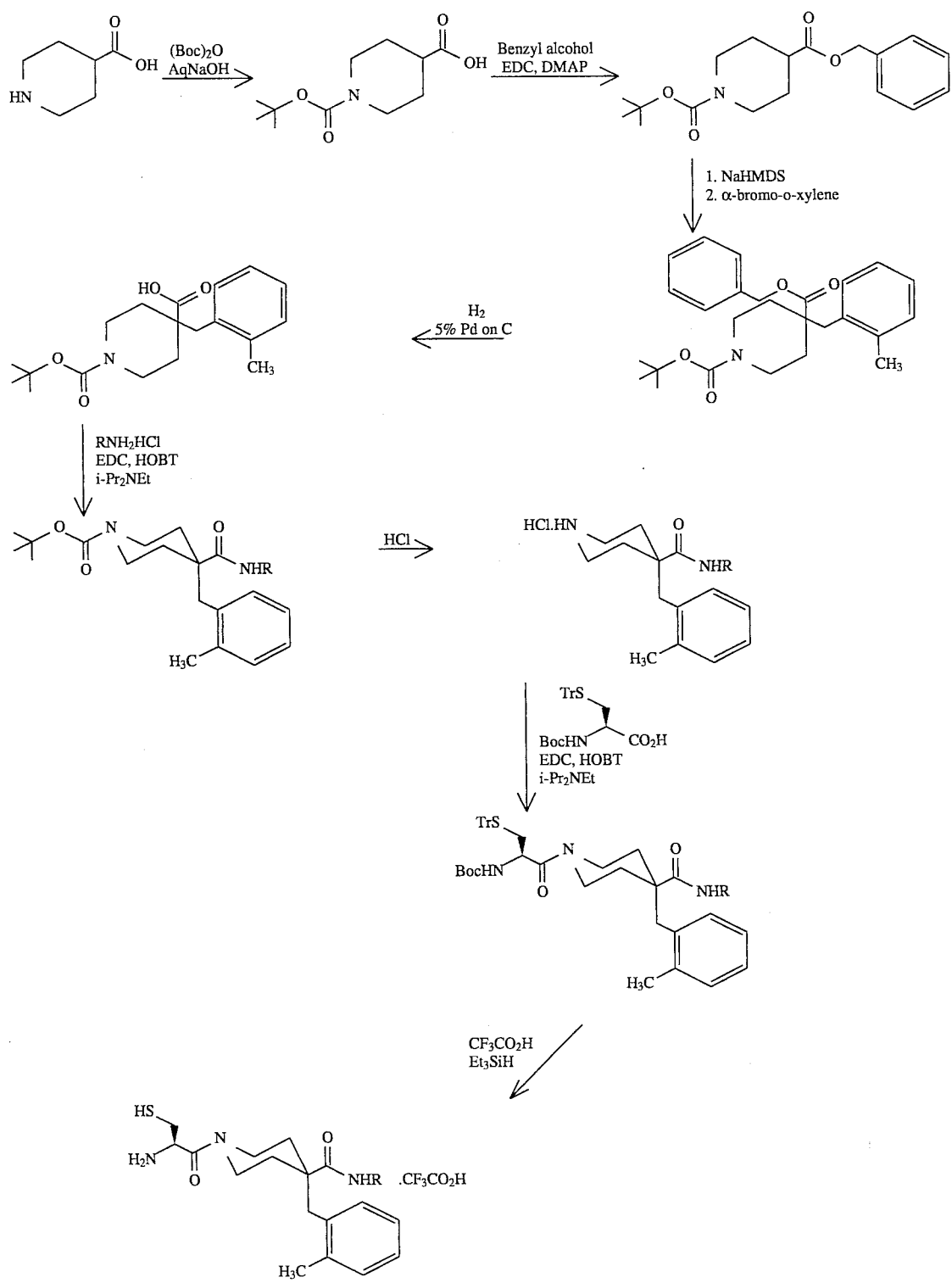
R = L-methionine methyl ester (8)

5,576,313
-continued
REACTION SCHEME 1
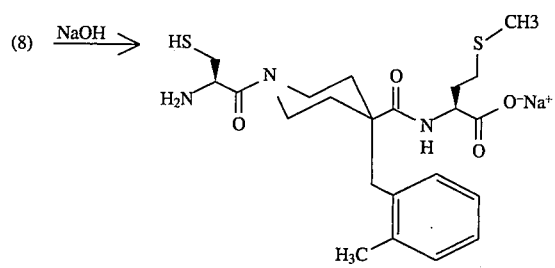
REACTION SCHEME 2
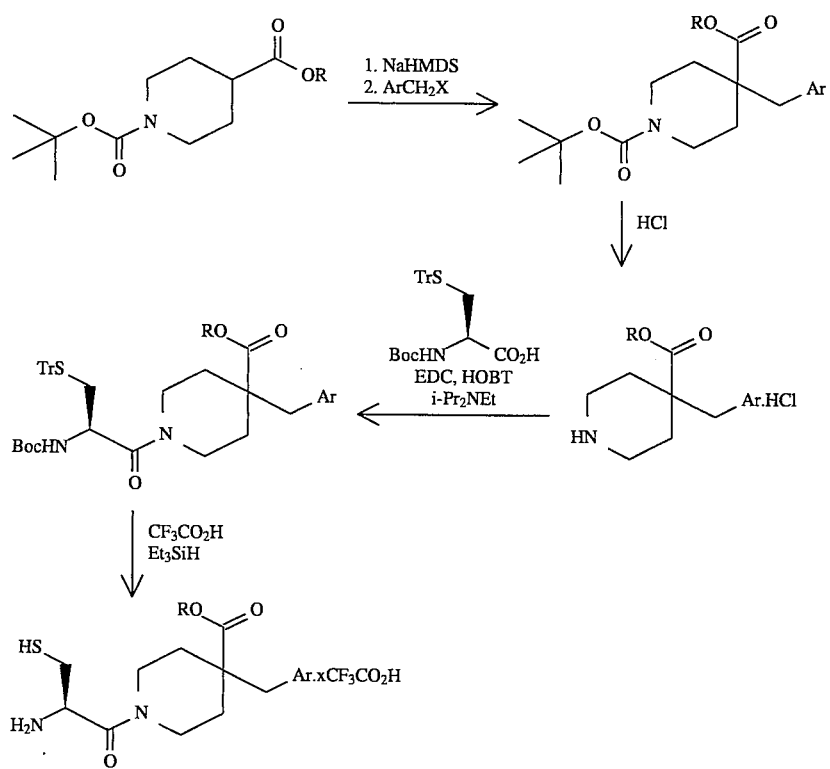
REACTION SCHEME 3
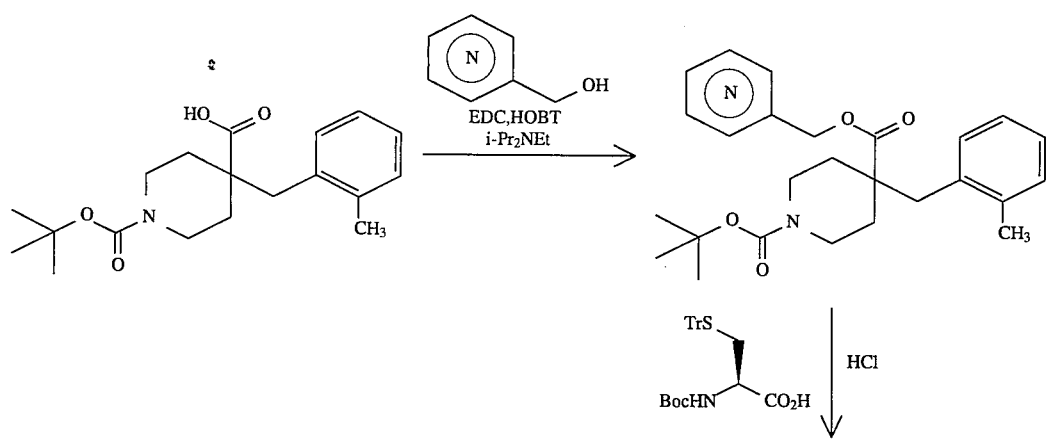

5,576,313
13 14
-continued
REACTION SCHEME 3
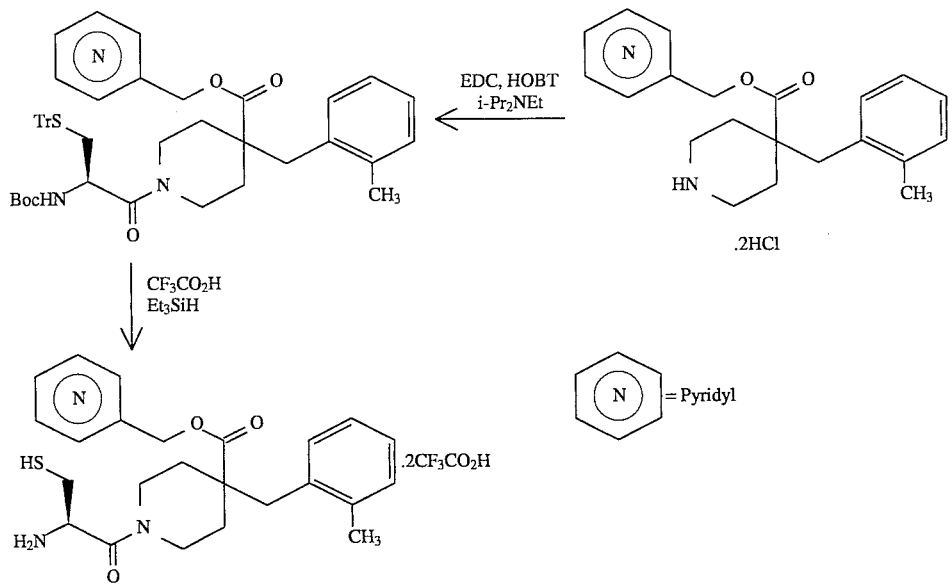
REACTION SCHEME 4
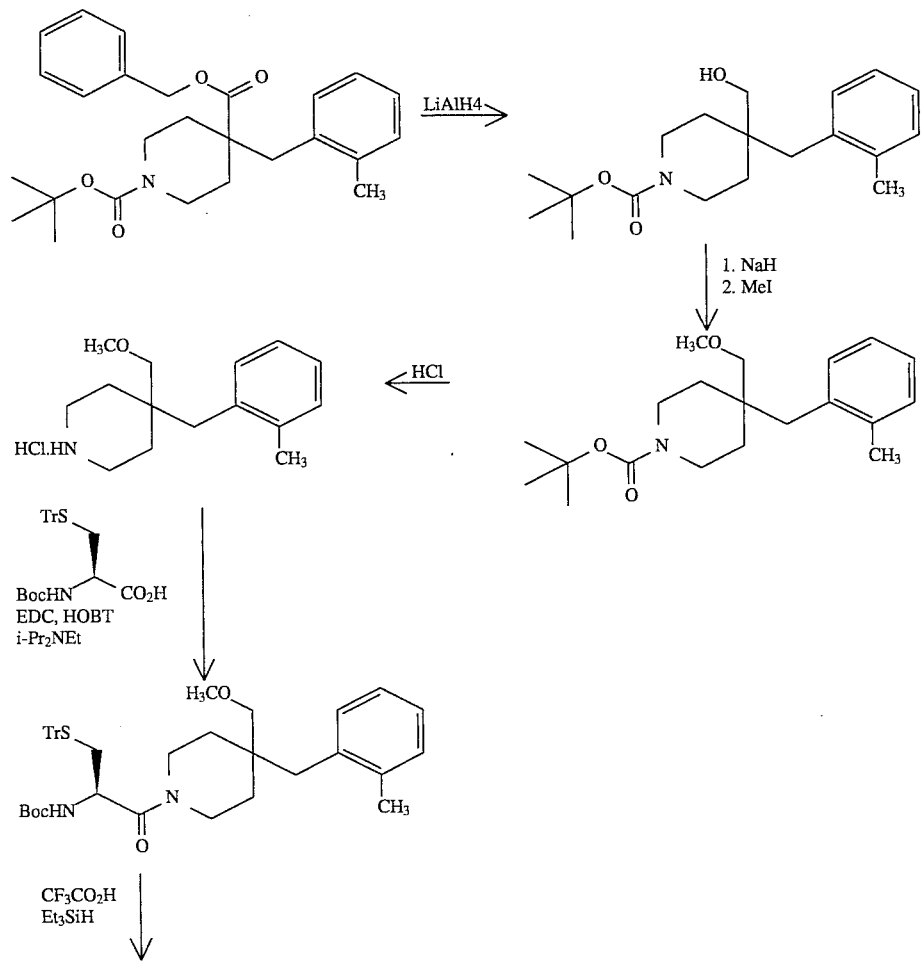

-continued
REACTION SCHEME 4
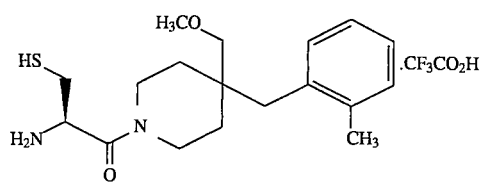
REACTION SCHEME 5
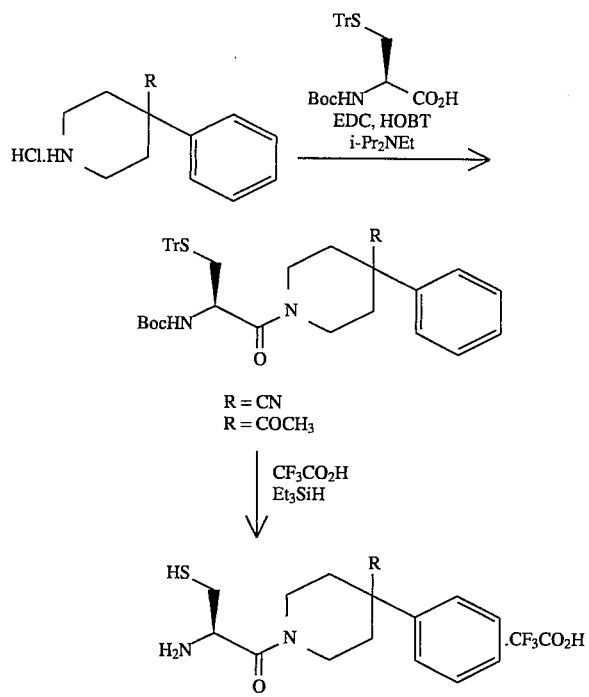
REACTION SCHEME 6
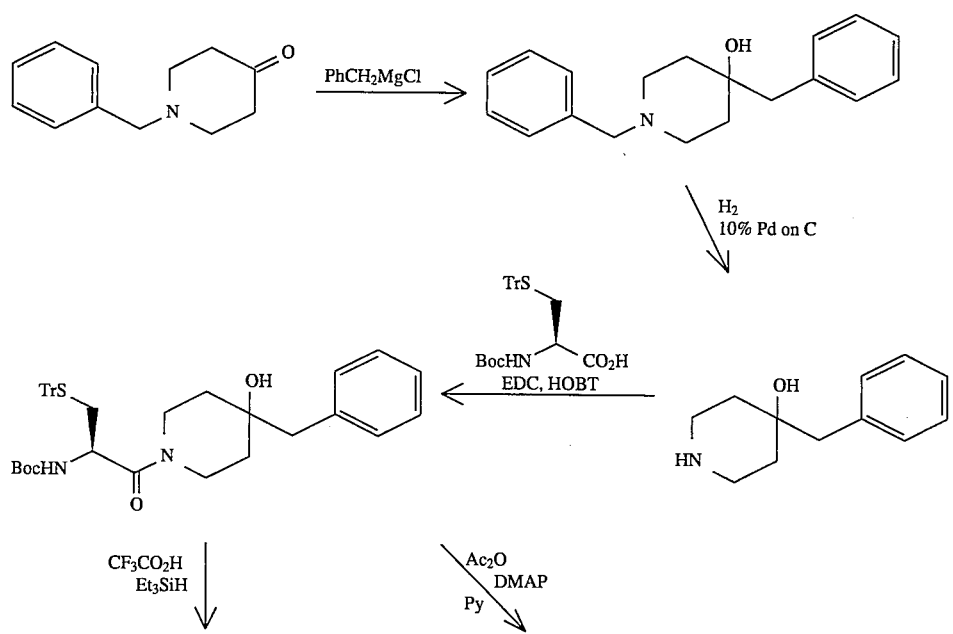

-continued
REACTION SCHEME 6
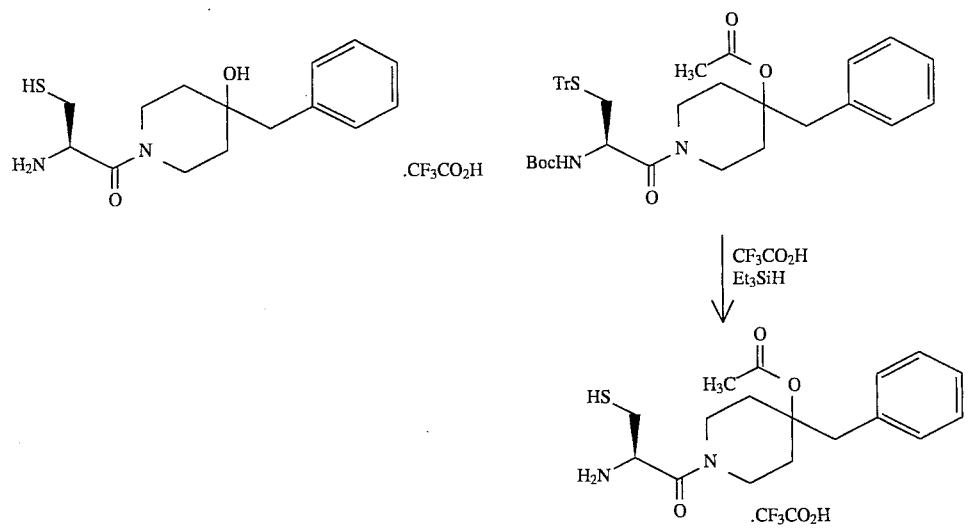
REACTION SCHEME 7
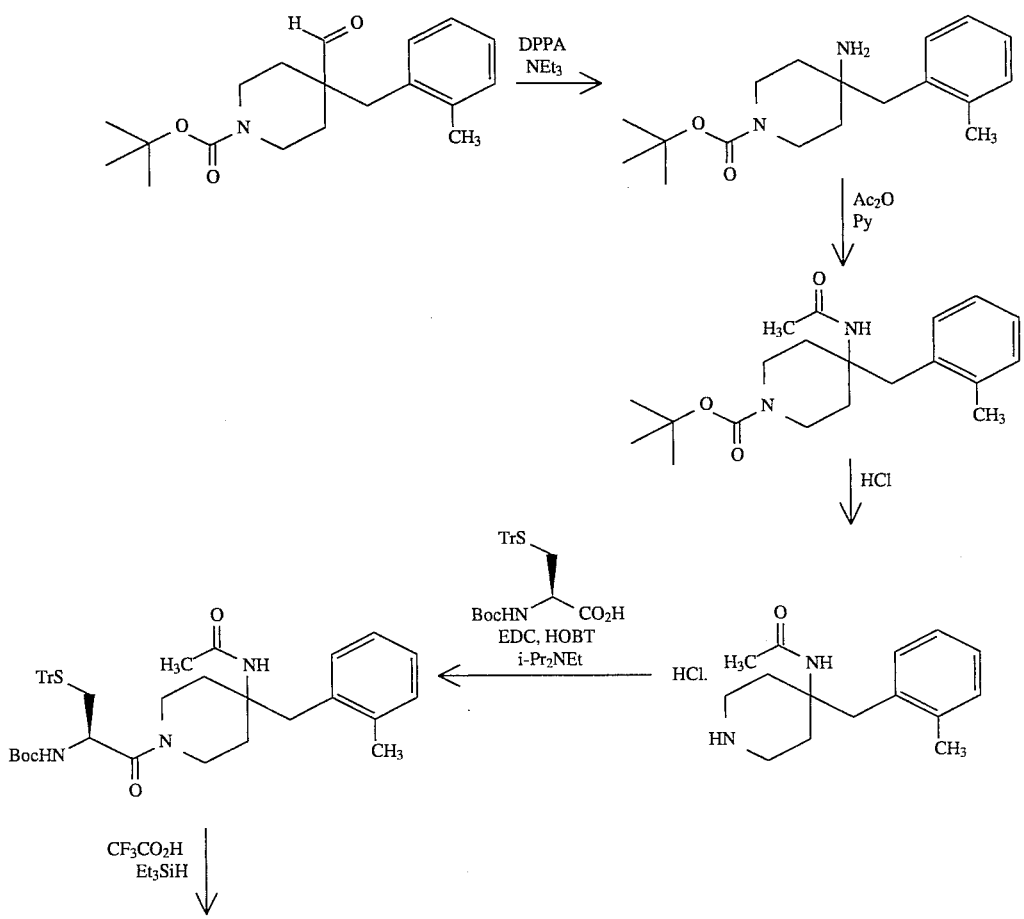

-continued
REACTION SCHEME 7

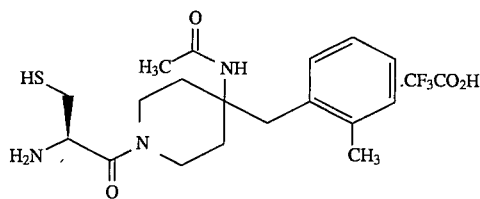

REACTION SCHEME 8

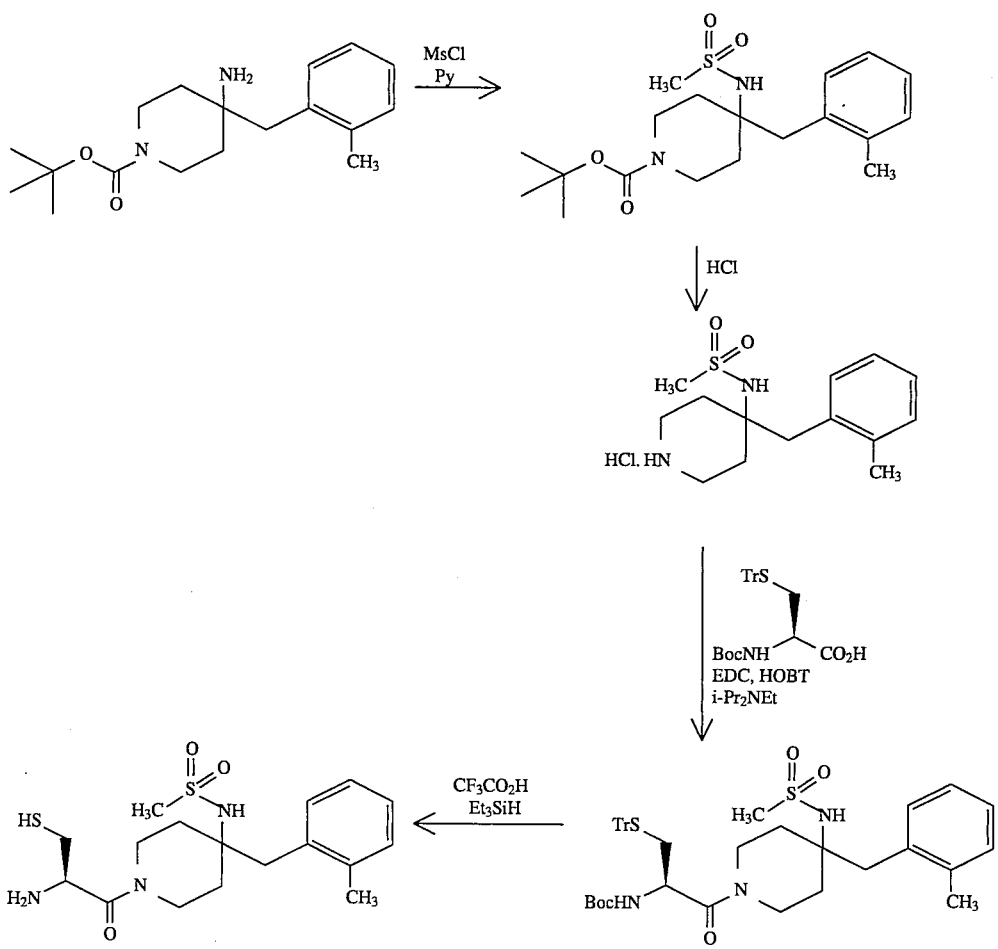

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

EXAMPLES

Examples provided are intended to assist in a further understanding of the invention. Particular materials, species and conditions employed are intended to be further illustrative of the invention and not limitative of the reasonable scope thereof.

EXAMPLE 1

L-Cysteinyl-4-(2-methylbenzyl)isonipecotyl-L-methionine

Step 1: Preparation of N-t-butoxycarbonyl isonipecotic acid

To a solution of isonipecotic acid (25.8 g, 200 mmol) in 1 M aqueous NaOH (223 ml, 223 mmol) was added a solution of di t-butyl dicarbonate in 200 ml THF over 1 hour. The resulting solution was stirred at room temp. overnight. The reaction mixture was then concentrated in vacuo to remove the THF and the residual aqueous solution extracted with hexane (2×125 ml). The hexane extracts were combined and back extracted with saturated NaHCO$_3$ (2×100 ml). All of the basic aqueous solutions were combined and cooled to 0° C. and then acidified with a 15% aqueous KHSO$_4$ solution to a pH of 1–2. The resulting thick slurry was extracted with EtOAc (4×), combined and washed with brine, dried over MgSO$_4$ and concentrated in vacuo to afford the product as a white solid.

Step 2: Preparation of N-t-butoxycarbonyl isonipecotic acid benzyl ester

To a solution of N-t-butoxycarbonyl isonipecotic acid (12.0 g, 52.3 mmol) in 100 ml of anhydrous CH$_2$Cl$_2$, was added benzyl alcohol (6.0 ml, 58 mmol), followed by 1-(3-dimethylamino-propyl)-3-ethylcarbodiimide hydrochloride (11.04 g, 57.6 mmol), and 4-dimethylaminopyridine (642 mg, 5.25 mmol). The resulting mixture was stirred for 6 hours then diluted with CH$_2$Cl$_2$ (150 ml) and washed successively with H$_2$O, 10% aqueous citric acid, saturated NaHCO$_3$, brine and then dried over MgSO$_4$. Concentration in vacuo afforded a colorless oil which was chromatographed on silica with 20% EtOAc/hexane as eluent. Appropriate fractions were combined and concentrated in vacuo to afford the product as a white solid.

Step 3: Preparation of N-t-butoxycarbonyl-4-(2-methylbenzyl) isonipecotic acid benzyl ester To a cold (−78° C.) solution of N-t-butoxycarbonyl isonipecotic acid benzyl ester (13.34 g, 41.8 mmol) in 140 ml of dry THF was added a 1.0 M THF solution of sodium bis trimethysilylamide (59 ml, 59 mmol) over 15 min. The resulting orange solution was stirred at −78° C. for 1 h and then treated dropwise with α-bromo-o-xylene (6.8 ml, 50.7 mmol) and then allowed to warm slowly to room temp. overnight. The reaction was quenched with saturated aqueous NH$_4$Cl, diluted with H$_2$O, and extracted with EtOAc (2×). The combined organic extracts were washed with brine (2×), and concentrated in vacuo to an orange gum. Flash chromatography on silica with 20% to 30% EtOAc/hexane as eluent, combining appropriate fractions, and concentrating in vacuo, afforded the product as a white solid.

Step 4: Preparation of N-t-butoxycarbonyl-4-(2-methylbenzyl) isonipecotic acid A mixture of 4-(2-methylbenzyl) N-t-butoxycarbonyl isonipecotic acid benzyl ester (2.36 g, 5.57 mmol), 5% Palladium on charcoal catalyst (250 mg), and glacial acetic acid (3 ml) in methanol (75 ml), was hydrogenated at 51 p.s.i. overnight, in a Parr shaker. The reaction mixture was then filtered through a pad of Celite and the pad washed several times with methanol. The combined filtrates were then concentrated in vacuo to the product, a white solid. 30 mg of this material was recrystallized from toluene to afford fine white crystals m.p. 176°–179° C. dec.

Step 5: Preparation of N-t-butoxycarbonyl-4-(2-methylbenzyl) isonipecotyl-L-methionine methyl ester A solution of the acid (302 mg, 0.91 mmol) in 5 ml DMF was treated in succession with 1-(3-dimethylaminopropyl)-3-ethylcarbodiimide hydrochloride (191 mg, 1.0 mmol), 1-hydroxybenzotriazole hydrate (135 mg, 1.0 mmol), L-methionine methyl ester hydrochloride (182 mg, 0.91 mmol), and diisopropylethylamine (0.17 ml, 1.0 mmol). The resulting mixture was stirred at room temp. overnight. The reaction solution was then concentrated in vacuo and partitioned between EtOAc and H$_2$O. The EtOAc layer was then washed with brine, dried over MgSO$_4$ and concentrated in vacuo to a light brown gum. This material was then chromatographed on silica with 30% EtOAc/hexane to afford, after combining and concentrating the appropriate fractions, the product as a colorless gum.

Step 6: Preparation of 4-(2-methylbenzyl)isonipecotyl-L-methionine methyl ester HCl salt A stream of anhydrous HCl gas was bubbled through a cold (0° C.) solution of (N-t-butoxycarbonyl-4-(2-methylbenzyl) isonipecotyl) L-methionine methyl ester (315 mg, 0.66 mmol) in 30 ml of EtOAc for 10 min. and the reaction solution stirred 1 h more at 0° C. The solution was then purged with argon for 10 min. and allowed to warm to room temp. Concentration of the solution in vacuo afforded the product as a colorless gum.

Step 7: Preparation of
N-t-butoxycarbonyl-S-trityl-L-Cysteinyl-4-
(2-methylbenzyl)isonipecotyl-L-methionine methyl
ester A solution of N-t-butoxycarbonyl-S-trityl-L-Cysteine (306 mg, 0.66 mmol), in 6 ml DMF under argon, was treated in succession with 1-(3-dimethylaminopropyl)-3-ethylcarbodiimide hydrochloride (132 mg, 0.69 mmol), 1-hydroxybenzotriazole hydrate (93 mg, 0.69 mmol), HCl salt (280 mg, 0.67 mmol), and diisopropylethylamine (0.12 ml, 0.69 mmol). The resulting mixture was stirred at room temp. overnight. The reaction solution was then concentrated in vacuo and partitioned between EtOAc and $H_2O$. The EtOAc layer was then washed with brine, dried over $MgSO_4$, and concentrated in vacuo to a light brown gum. This material was then chromatographed on silica with 40% EtOAc/ hexane to afford, after combining and concentrating the appropriate fractions, the product as a white foam.

Step 8: Preparation of
L-Cysteinyl-4-(2-methylbenzyl)isonipecotyl-
L-methionine methyl ester trifluoroacetic acid salt To a solution of methyl ester (75 mg, 0.09 mmol) in 2 ml $CH_2Cl_2$, was added trifluoroacetic acid (1 ml) followed by triethylsilane (0.059 ml, 0.36 mmol). The solution was stirred for 1.5 h at room temp. and then concentrated in vacuo. The residue was partitioned between a 0.1% aqueous trifluoroacetic acid solution (5 ml) and hexane. The aqueous layer was washed with hexane (4×) and then concentrated in vacuo to a gum. This material was then purified by preparative HPLC on a VYDAC $C^{18}$ protein and peptide column (22 mm diam.) and a 0.1% aqueous trifluoroacetic acid/ $CH_3CN$ mobile phase. The appropriate fractions were combined and lyophilized overnight to afford the product a white fluffy solid.

Anal. Calc'd for $C_{23}H_{35}N_3O_4S_2$ 1.30 $CF_3CO_2H$ 0.25 $H_2O$: C, 48.47; H, 5.85; N, 6.62. Found: C, 48.49; H, 5.83; N, 6.83.

Step 9: Hydrolysis of Me ester

A 10 mmolar solution of the hydrolyzed methyl ester was generated in situ for enzyme assay by treating a solution of methionine methyl ester (3.9 mg, 6.15 micromol), in methanol (0.050 ml), with a 1.0 M aqueous NaOH solution (0.024 ml, 24 micromol). After agitating for 30 sec. and standing at room temp for 2 h the solution was diluted with methanol (0.540 ml) to afford a 10 mmolar solution of the sodium salt of the hydrolyzed ester. The hydrolysis was monitored by HPLC for completeness.

EXAMPLE 2

L-Cysteinyl-4-(2-methylbenzyl)isonipecotyl
N-methyl amide trifluoroacetic acid salt Step 1: Preparation of
N-t-butoxycarbonyl-4-(2-methylbenzyl)
isonipecotyl-N-methyl amide A solution of N-t-butoxycarbonyl-4-(2-methylbenzyl) isonipecotic acid (167 mg, 0.50 mmol) in DMF (5 ml) was treated in succession with 1-(3-dimethylaminopropyl)-3-ethylcarbodiimide hydrochloride (105 mg. 0.55 mmol), 1-hydroxybenzotriazole hydrate (75 mg, 0.56 mmol), methylamine hydrochloride (38 mg, 0.56 mmol), and diisopropylethylamine (0.097 ml, 0.56 mmol). The resulting mixture was stirred at room temp. overnight. The reaction solution was then concentrated in vacuo and partitioned between EtOAc and $H_2O$. The EtOAc layer was isolated and the aqueous layer extracted with EtOAc (2×). The EtOAc extracts were combined and washed with brine, dried over $MgSO_4$, and concentrated in vacuo to a light brown gum. This material was then chromatographed on silica with 40% EtOAc/hexane to afford, after combining and concentrating the appropriate fractions, the product as a colorless gum.

Step 2: Preparation of
4-(2-methylbenzyl)isonipecotyl-N-methyl amide
hydrochloride salt The N-t-butoxycarbonyl deprotection procedure as described above in Example 1, Step 6 was utilized to afford the product as a white solid.

Step 3: Preparation of
N-t-butoxycarbonyl-S-trityl-L-Cysteinyl-4-
(2-methylbenzyl)isonipecotyl-N-methyl amide The coupling procedure as described above in Example 1, Step 7 was utilized to afford the product as a white foam.

Step 4: Preparation of
L-Cysteinyl-4-(2-methylbenzyl)isonipecotyl-N-methyl
amide trifluoroacetic acid salt Cysteine deprotection as described above in Example 1, Step 8 afforded the product as a white fluffy solid.

Anal. Calc'd for $C_{18}H_{27}N_3O_2S$ 1.25 $CF_3CO_2H$ 0.45 $H_2O$: C, 49.23; H, 5.87; N, 8.40. Found: C, 49.25; H, 5.87; N, 8.46.

EXAMPLE 3

L-Cysteinyl-4-(2-methylbenzyl)isonipecotyl
N-(2-pyridylmethyl) amide trifluoroacetic acid salt The titled compounds were prepared according to the methods of Example 2, substituting (2-aminomethyl) pyridine in Step 1. The amide bis trifluoroacetic acid salt was obtained as a white fluffy solid.

Anal. Calc'd for $C_{23}H_{30}N_4O_2S$ 2.25 $CF_3CO_2H$ 0.65 $H_2O$: C, 47.54; H, 4.87; N, 8.06. Found: C, 47.50; H, 4.87; N, 8.09.

EXAMPLE 4

L-Cysteinyl-4-(2-methylbenzyl)isonipecotyl
N-benzyl amide trifluoroacetic acid salt The titled compounds were prepared according to the methods of Example 2, substituting benzylamine in Step 1. The amide trifluoroacetic acid salt was obtained as a white fluffy solid.

Anal. Calc'd for $C_{24}H_{31}N_3O_2S$ 1.30 $CF_3CO_2H$ 0.50 $H_2O$: C, 54.82; H, 5.76; N, 7.21. Found: C, 54.83; H, 5.72; N, 7.30.

EXAMPLE 5

L-Cysteinyl-4-(2-methylbenzyl)isonipecotic acid methyl ester trifluoroacetic acid salt

Step 1: Preparation of N-t-butoxycarbonyl isonipecotic acid methyl ester

To an ice cold solution of N-t-butoxycarbonyl isonipecotic acid (8.8 g, 34.9 mmol), in a 10% mixture of methanol in benzene (250 ml), was added a 2.0 M solution of trimethylsilyldiazomethane in hexanes, dropwise, until a consistent yellow color was obtained (~30 ml). After vigorous gas evolution had ceased, cooling was removed and the reaction mixture stirred for 1 h at room temperature. The mixture was then treated dropwise with glacial acetic acid until all yellow color had dissipated. It was then stirred 15 min. and concentrated in vacuo to a pale yellow oil. This material was purified by column chromatography on silica with 20% EtOAc/hexane as eluent. The appropriate fractions were combined and concentrated in vacuo to afford the product as a colorless oil.

Step 2: Preparation of N-t-butoxycarbonyl-4-(2-methylbenzyl)isonipecotic acid methyl ester N-t-butoxycarbonyl isonipecotic acid methyl ester was transformed utilizing the alkylation procedure as described in Example 1, Step 3 substituting lithium diisopropylamide as the base to afford the product as a yellow syrup.

Step 3: Preparation of 4-(2-methylbenzyl)isonipecotic acid methyl ester HCl salt 4-(2-methylbenzyl) N-t-butoxycarbonyl isonipecotic acid methyl ester was deprotected as described above in Example 1, Step 6 to afford the product as a white solid.

Step 4: Preparation of N-t-butoxycarbonyl-S-trityl-L-Cysteinyl-4-(2-methylbenzyl)isonipecotic acid methyl ester The HCl salt was coupled to N-t-butoxycarbonyl-S-trityl-L-Cysteine utilizing the procedure described in Example 1, Step 7 to afford the product as a white foam.

Step 5: Preparation of L-Cysteinyl-4-(2-methylbenzyl)isoniopecotic acid methyl ester Trifluoroacetic acid salt The methyl ester was deprotected and purified as described in Example 1, Step 8 to afford the product as a white fluffy solid.

Anal. Calc'd for $C_{23}H_{35}N_3O_4S_2$ 1.30 $CF_3CO_2H$ 0.25 $H_2O$: C, 49.17; H, 5.57; N, 5.57. Found: C, 49.16; H, 5.55; N, 5.80.

EXAMPLE 6

L-Cysteinyl-4-benzyl isonipecotic acid methyl ester trifluoroacetic acid salt

The titled compounds were prepared according to the methods of Example 4, substituting benzyl bromide in Step 2. The methyl ester trifluoroacetic acid salt was obtained as a white fluffy solid.

Anal. Calc'd for $C_{17}H_{24}N_2O_3S$ 1.20 $CF_3CO_2H$: C, 49.23; H, 5.37; N, 5.92. Found: C, 48.91; H, 5.28; N, 5.94.

EXAMPLE 7

L-Cysteinyl-4-(2-chlorobenzyl)isonipecotic acid methyl ester trifluoroacetic acid salt The titled compounds were prepared according to the methods of Example 4, substituting 2-chlorobenzyl bromide in Step 2. The methyl ester trifluoroacetic acid salt was obtained as a white fluffy solid.

Anal. Calc'd for $C_{17}H_{23}ClN_2O_3S$ 1.40 $CF_3CO_2H$: C, 44.83; H, 4.64; N, 5.28. Found: C, 44.64; H, 4.66; N, 5.30.

EXAMPLE 8

L-Cysteinyl-4-(2,3-dichlorobenzyl)isonipecotic acid methyl ester trifluoroacetic acid salt The titled compounds were prepared according to the methods of Example 4, substituting 2,3-dichlorobenzyl bromide (prepared from 2,3-dichlorotoluene according to the procedure described in *J. Chem. Res.* (S) (1984) 24.) in Step 2. The methyl ester trifluoroacetic acid salt was obtained as a white solid.

Anal. Calc'd for $C_{17}H_{22}N_2O_3S$ 1.55 $CF_3CO_2H$ 0.15 $H_2O$: C, 41.28; H, 4.11; N, 4.79. Found: C, 41.26; H, 4.09; N, 5.11.

EXAMPLE 9

L-Cysteinyl-4-(2,4-dichlorobenzyl)isonipecotic acid methyl ester trifluoroacetic acid salt The titled compounds were prepared according to the methods of Example 4, substituting α, 2,4-trichlorotoluene in Step 2. The methyl ester trifluoroacetic acid salt was obtained as a white solid.

Anal. Calc'd for $C_{17}H_{22}N_2O_3S$ 1.55 $CF_3CO_2H$: C, 41.48; H, 4.08; N, 4.81. Found: C, 41.51; H, 4.08; N, 4.98.

EXAMPLE 10

L-Cysteinyl-4-(2,6-dichlorobenzyl)isonipecotic acid methyl ester trifluoroacetic acid salt The titled compounds were prepared according to the methods of Example 4, substituting α, 2,6-trichlorotoluene in Step 2. The methyl ester trifluoroacetic acid salt was obtained as a white fluffy solid.

Anal. Calc'd for $C_{17}H_{22}N_2O_3S$ 1.25 $CF_3CO_2H$ 0.15 $H_2O$: C, 42.54; H, 4.31; N, 5.09. Found: C, 42.55; H, 4.30; N, 5.11.

EXAMPLE 11

L-Cysteinyl-4-(3-(2-methyl)pyridylmethyl)isonipecotic acid methyl ester trifluoroacetic acid salt The titled compounds were prepared according to the methods of Example 4, substituting 3-(chloromethyl)-2-methyl pyridine (preparation described below). The methyl ester bis trifluoroacetic acid salt was obtained as a colorless gum.

Anal. Calc'd for $C_{17}H_{25}N_3O_3S$ 1.45 $CF_3CO_2H$ 0.30 $H_2O$: C, 41.34; H, 4.44; N, 6.60. Found: C, 41.33; H, 4.44; N, 6.74.

Preparation of 3-(Chloromethyl)-2-methyl pyridine

Step 1: Preparation of 3-hydroxymethy-2-methylpyridine

To a suspension of lithium aluminum hydride (2.0 g, 53 mmol) in anhydrous ether (300 ml) was added a solution of methyl-2-methylpyridine carboxylate (8.14 g, 53.8 mmol) in 100 ml anhydrous ether over 20 min. The reaction mixture was stirred 1.5 h at room temp. and the treated carefully in succession with 2 ml of water, 2 ml of 15% aqueous sodium hydroxide, and 6 ml of water. The white slurry was stirred 1 h at room temp. and then filtered through Celite. After several washings with ether, the combined filtrates were washed with brine, dried (MgSO$_4$), and concentrated in vacuo to a pale yellow oil. This material was purified by column chromatography on silica with 5% methanol/chloroform as eluent to afford the product as a colorless oil.

Step 2: Preparation of 3-chloromethyl-2-methylpyridine

To a solution of 3-hydroxymethy-2-methylpyridine (0.65 g, 5.3 mmol) in dry benzene (5 ml) was added triethylamine (1.0 ml, 7.4 mmol) followed by methanesulfonyl chloride (0.78 ml, 10.1 mmol) dropwise over 5 min. The heterogeneous dark gummy mixture was stirred at room temp. overnight. The reaction was filtered through Celite and washed with benzene (2×). The combined filtrates were washed with brine, dried (Na$_2$SO$_4$), and concentrated in vacuo to the crude product as a yellow oil which was used as is.

EXAMPLE 12

L-Cysteinyl-4-(1-naphthyl)methyl isonipecotic acid methyl ester trifluoroacetic acid salt The titled compounds were prepared according to the methods of Example 4, substituting 1-(bromomethyl) naphthalene (preparation described below) and lithium diisopropylamide as the base in Step 2. The methyl ester trifluoroacetic acid salt was obtained as a white fluffy solid.

Anal. Calc'd for C$_{21}$H$_{26}$N$_2$O$_3$S 1.25 CF$_3$CO$_2$H 0.95 H$_2$O: C, 51.68; H, 5.38; N, 5.13. Found: C, 51.64; H, 5.43; N, 5.14.

Preparation of 1-(bromomethyl) naphthalene

To a suspension of triphenylphosphine (10.5 g, 40 mmol) and carbon tetrabromide (13.3 g, 40 mmol) in anhydrous ether (200 ml) was added 1-naphthylmethanol (5.28 g, 33.4 mmol). The mixture was stirred at room temp. for 2 h and then concentrated in vacuo to a pale orange oil. This material was triturated with hexane and the resulting pale orange solid removed via filtration. The solid was washed several times with hexane and the combined filtrates from the washings passed through a short column of Florisil. Concentration in vacuo of the eluent afforded the bromide as a pale yellow solid.

EXAMPLE 13

L-Cysteinyl-4-(1-naphthyl)methyl isonipecotic acid ethyl ester trifluoroacetic acid salt The titled compounds were prepared according to the methods of Example 4, utilizing N-t-butoxycarbonyl isonipecotic acid ethyl ester and alkylating with 1-(bromomethyl) naphthalene and lithium diisopropylamide as the base in Step 2. The ethyl ester trifluoroacetic acid salt was obtained as a white fluffy solid.

Anal. Calc'd for C$_{22}$H$_{28}$N$_2$O$_3$S 1.05 CF$_3$CO$_2$H 0.25 H$_2$O: C, 55.16; H, 5.68; N, 5.34. Found: C, 55.13; H, 5.72; N, 5.20.

EXAMPLE 14

L-Cysteinyl-4-(1-naphthyl)methyl isonipecotic acid benzyl ester trifluoroacetic acid salt The titled compounds were prepared according to the methods of Example 4, utilizing N-t-butoxycarbonyl isonipecotic acid benzyl ester and alkylating with 1-(bromomethyl) naphthalene and lithium diisopropylamide as the base in Step 2. The benzyl ester trifluoroacetic acid salt was obtained as a white fluffy solid.

Anal. Calc'd for C$_{27}$H$_{30}$N$_2$O$_3$S 1.30 CF$_3$CO$_2$H: C, 58.20; H, 5.16; N, 4.59. Found: C, 58.25; H, 5.18; N, 4.94.

EXAMPLE 15

L-Cysteinyl-4-(2-methylbenzyl)isonipecotic acid 2-pyridylmethyl ester trifluoroacetic acid salt

Step 1: Preparation of N-t-butoxycarbonyl-4-(2-methylbenzyl) isonipecotic acid 2-pyridylmethyl ester To a solution of N-t-butoxycarbonyl-4-(2-methylbenzyl) isonipecotic acid (666 mg, 2.0 mmol) in dry CH$_2$Cl$_2$ (15 ml) was added 1-(3-dimethylaminopropyl)-3-ethylcarbodiimide hydrochloride (421 mg. 2.2 mmol). After stirring 15 min., 2-pyridine carbinol (0.21 ml, 2.2 mmol) and 4-dimethylaminopyridine (244 mg, 2.0 mmol) were added and the reaction mixture stirred at room temp. overnight. The reaction mixture was then adsorbed directly onto a small amount of silica and chromatographed with 30% EtOAc/hexane as eluent. The appropriate fractions were combined and concentrated in vacuo to afford the product as a colorless gum.

Step 2: Preparation of 4-(2-methylbenzyl)isonipecotic acid 2-pyridylmethyl ester bis HCl salt N-t-butoxycarbonyl-4-(2-methylbenzyl)isonipecotic acid 2-pyridylmethyl ester was deprotected as described above in Example 1, Step 6 to afford the product as a white hygroscopic solid.

Step 3: Preparation of N-t-butoxycarbonyl-S-trityl-L-Cysteinyl-4-(2-methylbenzyl)isonipecotic acid 2-pyridylmethyl ester 4-(2-methylbenzyl)isonipecotic acid 2-pyridylmethyl ester bis HCl salt was coupled to N-t-butoxycarbonyl-S-trityl-L-Cysteine utilizing the procedure described in Example 1, Step 7 to afford the product as a white foam.

Step 4: Preparation of L-Cysteinyl-4-(2-methylbenzyl)isonipecotic acid 2-pyridylmethyl ester bis trifluoroacetic acid salt N-t-butoxycarbonyl-S-trityl-L-Cysteine 4-(2-methylbenzyl)isonipecotic acid 2-pyridylmethyl ester was deprotected and purified as described in Example 1, Step 8 to afford the product as a white fluffy solid.

Anal. Calc'd for $C_{23}H_{29}N_3O_3S$ 2.80 $CF_3CO_2H$ 0.20 $H_2O$: C, 45.78; H, 4.33; N, 5.60. Found: C, 45.78; H, 4.33; N, 5.87.

EXAMPLE 15(a).

L-Cysteinyl-4-(2-methylbenzyl)isonipecotic acid 3-pyridylmethyl ester trifluoroacetic acid salt The titled compounds were prepared according to the methods of Example 15, substituting 3-pyridine carbinol. The methyl ester bis trifluoroacetic acid salt was obtained.

Anal. Calc'd for $C_{23}H_{29}N_3O_3S$ 2.35 $CF_3CO_2H$ 0.40 $H_2O$: C, 47.35; H, 4.61; N, 5.98. Found: C, 47.33; H, 4.63; N, 6.06.

EXAMPLE 15(b)

L-Cysteinyl-4-(2-methylbenzyl)isonipecotic acid 4-pyridylmethyl ester trifluoroacetic acid salt The titled compounds were prepared according to the methods of Example 15, substituting 4-pyridine carbinol. The methyl ester bis trifluoroacetic acid salt was obtained.

Anal. Calc'd for $C_{23}H_{29}N_3O_3S$ 2.10 $CF_3CO_2H$ 1.70 $H_2O$: C, 46.83; H, 4.98; N, 6.02. Found: C, 46.83; H, 5.02; N, 6.03.

EXAMPLE 16

L-Cysteinyl-4-benzyl-4-piperidinol trifluoroacetic acid salt

Step 1: Preparation of N-benzyl-4-benzyl-4-piperidinol

To a solution of benzyl magnesium chloride (40 ml of 2.0 M soln. in THF, 80 mmol) in THF (80 ml) was added 1-benzyl-4-piperidinone (7.4 ml, 40 mmol) over 7 min. and stirred overnight. The o reaction mixture was poured over ice and extracted with ether (2×). The combined ether extracts were washed with brine, dried ($Na_2SO_4$), and concentrated in vacuo to a pale green syrup. This material was chromatographed on silica with 50–60% EtOAc/hexane as eluent. The appropriate fractions were combined and concentrated in vacuo to afford the product as an off white solid.

Step 2: Preparation of 4-Benzyl-4-piperidinol

A mixture of N-benzyl-4-benzyl-4-piperidinol (2.0 g, 7.1 mmol) and 10% palladium on charcoal catalyst (0.5 g) in absolute ethanol (100 ml), was stirred vigorously at 40° C. under a balloon of hydrogen for 5 h. The reaction mixture was then filtered through a pad of Celite and the filtrate concentrated in vacuo to a grayish solid. This material was dissolved in methanol and filtered a second time through Celite and the filtrate concentrated in vacuo to the product, a white solid.

Step 3: Preparation of N-t-butoxycarbonyl-S-trityl-L-Cysteinyl-4-benzyl-4-piperidinol The coupling procedure as described above in Example 1, Step 7 was utilized, with the amendment that no amine base was added, to afford the product as a white foam.

Step 4: Preparation of L-Cysteinyl-4-benzyl-4-piperidinol

Cysteine deprotection as described above in Example 1, Step 8 afforded the product as a white solid.

Anal. Calc'd for $C_{15}H_{22}N_2O_2S$ 1.30 $CF_3CO_2H$ 0.05 $H_2O$: C, 47.66; H, 5.32; N, 6.32. Found: C, 47.68; H, 5.32; N, 6.32.

EXAMPLE 17

L-Cysteinyl-4-acetoxy-4-benzylpiperidine trifluoroacetic acid salt

Step 1: Preparation of N-t-butoxycarbonyl-S-trityl-L-Cysteine-4-acetoxy-4-benzylpiperidine To a solution of N-t-butoxycarbonyl-S-trityl-L-Cysteinyl4-benzyl-4-piperidinol (100 mg, 0.16 mmol) in dry pyridine (2 ml), was added 4-dimethylaminopyridine (25 mg, 0.20 mmol) and acetic anhydride (0.030 ml, 0.32 mmol). The solution was heated to 50° C. (oil bath temp.) for 2 days and then allowed to cool to room temp. The reaction mixture was concentrated in vacuo and the residue partitioned between EtOAc and brine. The EtOAc layer was dried ($MgSO_4$) and concentrated in vacuo to a brown oil. This material was purified by column chromatography on silica with 18–20% EtOAc/hexane as eluent. The appropriate fractions were combined and concentrated in vacuo to afford the product as a glassy solid.

Step 2: Preparation of L-Cysteinyl-4-acetoxy-4-benzylpiperidine

Cysteine deprotection as described above in Example 1, Step 8 afforded the product as a white fluffy solid.

Anal. Calc'd for $C_{17}H_{24}N_2O_3S$ 1.15 $CF_3CO_2H$ 0.40 $H_2O$: C, 48.73; H, 5.52; N, 5.89. Found: C, 48.75; H, 5.48; N, 6.16.

EXAMPLE 18

L-Cysteinyl-4-cyano-4-phenylpiperidine trifluoroacetic acid salt

Step 1: Preparation of N-t-butoxycarbonyl-S-trityl-L-Cysteinyl-4-cyano-4-phenylpiperidine The coupling procedure as described above in Example 1, Step 7 was utilized, with commercially available 4-phenyl-4-cyano-piperidine hydrochloride salt, to afford the product as a white foam.

Step 2: Preparation of L-Cysteinyl-4-cyano 4-phenylpiperidine

Cysteine deprotection as described above in Example 1, Step 8 afforded the product as a white solid.

Anal. Calc'd for $C_{15}H_{19}N_3OS$ 1.20 $CF_3CO_2H$ 0.15 $H_2O$: C, 48.72; H, 4.82; N, 9.80. Found: C, 48.78; H, 4.81; N, 9.75.

EXAMPLE 19

L-Cysteinyl-4-acetyl-4-phenylpiperidine trifluoroacetic acid salt

Step 1: Preparation of N-t-butoxycarbonyl-S-trityl-L-Cysteinyl-4-acetyl-4-phenylpiperidine The coupling procedure as described above in Example 1, Step 7 was utilized, with commercially available 4-acetyl-4-phenyl-piperidine hydrochloride salt, to afford the product as a white foam.

Step 2: Preparation of L-Cysteinyl-4-acetyl-4-phenylpiperidine

Cysteine deprotection as described above in Example 1, Step 8 afforded the product as a white solid.

Anal. Calc'd for $C_{16}H_{22}N_2O_2S$ 1.45 $CF_3CO_2H$: C, 48.12; H, 5.01; N, 5.94. Found: C, 48.02; H, 5.06; N, 5.96.

EXAMPLE 20

L-Cysteinyl-4-methoxymethyl-4-(2-methylbenzyl)piperidine trifluoroacetic acid salt

Step 2: Preparation of N-t-Butoxycarbonyl-4-hydroxymethyl-4-(2-methylbenzyl)piperidine To a suspension of lithium aluminum hydride (0.32 g, 8.4 L s mmol) in anhydrous ether (50 ml) was added a solution of 4-(2-methylbenzyl) N-t-butoxycarbonyl isonipecotic acid benzyl ester (3.0 g, 7.1 mmol) in anhydrous ether (25 ml) over 15 min. The resulting mixture was heated gently at reflux for 1 h. The reaction mixture was then quenched with the slow and successive addition of $H_2O$ (0.32 ml), 15% aqueous NaOH, and $H_2O$ (0.96 ml). After sirring for 30 min., the mixture was filtered through Celite and the filtrate washed with brine, dried ($MgSO_4$), and concentrated in vacuo to a colorless syrup. Purification by column chromatography on silica with 25%–50% EtOAc/hexane as eluent afforded the product as a colorless gum. This material was recrystallized from EtOAc and hexane to afford a white solid. m.p. 104°–106° C.

Step 2: Preparation of N-t-Butoxycarbonyl-4-methoxymethyl-4-(2-methylbenzyl)piperidine To a 0° C. suspension of sodium hydride (19 mg, 0.80 mmol) in 1.5 ml of THF, was added a solution of N-t-butoxycarbonyl-4-hydroxymethyl-4-(2-methylbenzyl)piperidine (200 mg, 0.63 mmol) in 1 ml THF. The mixture was allowed to warm to room temp. To this suspension was added 0.35 ml of anhydrous DMSO and the mixture was heated to 60° C. and stirred 5 h until the solution was almost homogeneous. The reaction mixture was allowed to cool to room temp. and to this solution was added methyl iodide (0.070 ml, 1.12 mmol). The resulting heterogeneous mixture was stirred at room temp. overnight. The reaction mixture was treated with 10% aqueous citric acid and extracted with ether (3×). The combined ether extracts were washed successively with saturated aqueous $NaHCO_3$ and brine, dried ($MgSO_4$), and concentrated in vacuo to a yellow gum. Purification by column chromatography on silica with 9% EtOAc/hexane as eluent afforded the product as a colorless gum.

Step 2: Preparation of 4-Methoxymethyl-4-(2-methylbenzyl)-piperidine HCl salt N-t-Butoxycarbonyl-4-methoxymethyl-4-(2-methylbenzyl) piperidine was deprotected as described above in Example 1, Step 6 to afford the product as a white solid.

Step 3: Preparation of N-t-butoxycarbonyl-S-trityl-L-Cysteinyl-4-methoxymethyl-4-(2-methylbenzyl)piperidine The coupling procedure as described above in Example 1, Step 7 was utilized to afford the product as a white foam.

Step 4: Preparation of L-Cysteinyl-4-methoxymethyl-4-(2-methylbenzyl)piperidine Cysteine deprotection as described above in Example 1, Step 8 afforded the product as a white solid.

Anal. Calc'd for $C_{18}H_{28}N_2O_2S$ 1.25 $CF_3CO_2H$ 0.20 $H_2O$: C, 51.02; H, 6.19; N, 5.80. Found: C, 50.97; H, 6.19; N, 6.04.

EXAMPLE 21

L-Cysteinyl-4-acetamido-4-(2-methylbenzyl)piperidine trifluoroacetic acid salt

Step 1: Preparation of N-t-butoxycarbonyl-4-amino-4-(2-methylbenzyl)piperidine To a mixture of 4-(2-methylbenzyl) N-t-butoxycarbonyl isonipecotic acid (1.0 g, 3.0 mmol) in $CH_3CN$ (20 ml) add diphenyl phosphoryl azide (0.99 g, 3.6 mmol) and triethylamine (0.50 ml, 3.6 mmol). After stirring at 55° C. (oil bath temp.) concentrate the reaction in vacuo and partion the residue between EtOAc and saturated aqueous $NaHCO_3$. The organic phase is washed with brine, dried ($MgSO_4$), and concentrated in vacuo to afford the crude product.

Step 2: Preparation of N-t-butoxycarbonyl-4-acetamido-4-(2-methylbenzyl)piperidine A mixture of N-t-butoxycarbonyl-4-amino-4-(2-methylbenzyl)piperidine (305 mg, 1.0 mmol), acetic anhydride (0.38 ml, 4.0 mmol), and pyridine (0.1 ml, 1.2 mmol) in $CH_2Cl_2$ is stirred at room temp. overnight. Then concentrate the reaction mixture in vacuo and purify the residue by column chromatography on silica to afford the product.

Step 3: Preparation of 4-Acetamido-4-(2-methylbenzyl)piperidine hydrochloride salt The N-t-butoxycarbonyl deprotection procedure as described above in Example 1, Step 6 is utilized to afford the product.

Step 4: Preparation of N-t-butoxycarbonyl-S-trityl-L-Cysteinyl-4-acetamido-4-(2-methylbenzyl)piperidine The coupling procedure as described above in Example 1, Step 7 is utilized to afford the product.

Step 5: Preparation of
L-Cysteinyl-4-acetamido-4-(2-methylbenzyl)piperidine trifluoroacetic acid salt Cysteine deprotection as described above in Example 1, Step 8 affords the product.

EXAMPLE 22

L-Cysteinyl-4-methylsulfonamido-4-(2-methylbenzyl)piperidine trifluoroacetic acid salt

Step 1: Preparation of
N-t-butoxycarbonyl-4-methylsulfonamido-4-(2-methylbenzyl)piperidine A mixture of N-t-butoxycarbonyl-4-amino-4-(2-methylbenzyl)piperidine (305 mg, 1.0 mmol), methane-sulfonyl chloride (0.31 ml, 4.0 mmol), and pyridine (0.1 ml, 1.2 mmol) in $CH_2Cl_2$ (2 mL) is stirred at room temp. overnight. Then concentrate the reaction mixture in vacuo and purify the residue by column chromatography on silica to afford the product.

Step 2: Preparation of
4-Methylsulfonamido-4-(2-methylbenzyl) piperidine hydrochloride salt The N-t-butoxycarbonyl deprotection procedure as described above in Example 1, Step 6 is utilized to afford the product.

Step 3: Preparation of
N-t-butoxycarbonyl-S-trityl-L-Cysteinyl-4-methylsulfonamido-4-(2-methylbenzyl)piperidine The coupling procedure as described above in Example 1, Step 7 is utilized to afford the product.

Step 4: Preparation of
L-Cysteinyl-4-methylsulfonamido-4-(2-methylbenzyl)piperidine trifluoroacetic acid salt Cysteine deprotection as described above in Example 1, Step 8 affords the product.

EXAMPLE 23

In vitro inhibition of ras farnesyl transferase

Farnesyl-protein transferase (FTase) from bovine brain was chromatographed on DEAE-Sephacel (Pharmacia, 0–0.8 M NaCl gradient elution), N-octyl agarose (Sigma, 0–0.6 M NaCl gradient elution), and a mono Q HPLC column (Pharmacia, 0–0.3 M NaCl gradient). Ras-CVLS at 3.5 μM, 0.25 μM [$^3$H]FPP, and the indicated compounds were incubated with either a partially purified bovine enzyme preparation or a recombinant human enzyme preparation. The recombinant human enzyme was prepared as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. The FTase data presented reflects the ability of the test compound to inhibit RAS farnesylation in vitro, as described in Pompliano, et al., *Biochemistry* 31:3800 (1992).

In the above assay, the compounds, as listed on pages 6–8, demonstrated the ability to inhibit RAS farnesylation at a concentration of 10 μM or less. For the preferred compounds, listed on pages 8 to 9, activity was exhibited at 2 μM or less.

What is claimed is:

1. A compound which inhibits farnesyl-protein transferase of the Formula I:

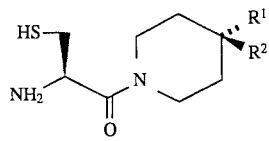

wherein:
$R^1$ is selected from:
a) COR,
b) $CO_2R$,
c) CONHR,
d) OH,
e) OCOR,
f) CN,
g) $CH_2OR$,
h) NHCOR,
i) $NHSO_2R$, or
j) $COR^5$;
R is selected from:
a) $C_{1-4}$ alkyl, unsubstituted or substituted with:
  i) $C_{1-4}$ alkoxy,
  ii) $NR^3R^4$,
  iii) $C_{3-6}$ cycloalkyl,
  iv) aryl or heterocycle; or
b) aryl or heterocycle;
$R^2$ is selected from: aryl, aralkyl, heterocycle, or heteroaralkyl, unsubstituted or substituted with one or more of:
a) $C_{1-4}$ alkyl, unsubstituted or substituted with:
  i) $C_{1-4}$ alkoxy,
  ii) $NR^3R^4$,
  iii) $C_{3-6}$ cycloalkyl, or
  iv) aryl or heterocycle;
b) aryl or heterocycle,
c) halogen,
d) $OR^3$,
e) $NR^3R^4$,
f) CN,
g) $NO_2$, or
h) $CF_3$;
$R^3$ and $R^4$ are independently selected from: H, $C_{1-4}$ alkyl, $C_{3-6}$ cycloalkyl, heterocycle, aryl, aroyl, heteroaryl, arylsulfonyl, heteroarylsulfonyl, unsubstituted or substituted with one or more of:
a) $C_{1-4}$ alkoxy,
b) aryl or heterocycle,
c) halogen, or
d) HO, wherein
or $R^3$ and $R^4$ may be joined in a ring;
$R^5$ is selected from:
a) a naturally occurring amino acid, or
b) an oxidized form of a naturally occurring amino acid which is:
  i) methionine sulfoxide, or
  ii) methionine sulfone;
or the pharmaceutically acceptable salt thereof.

2. A compound according to claim 1 which is selected from the group consisting of:
L-Cysteinyl-4-(2-methylbenzyl)isonipecotyl-L-methionine;

L-Cysteinyl-4-benzyl isonipecotic acid methyl ester;
L-Cysteinyl-4-(2-methylbenzyl)isonipecotyl N-methyl amide;
L-Cysteinyl-4-(2-methylbenzyl)isonipecotyl N-(2-pyridylmethyl) amide;
L-Cysteinyl-4-(2-methylbenzyl)isonipecotyl N-benzyl amide;
L-Cysteinyl-4-(2-methylbenzyl)isonipecotic acid methyl ester;
L-Cysteinyl-4-(2-chlorobenzyl)isonipecotic acid methyl ester;
L-Cysteinyl-4-(2,3-dichlorobenzyl)isonipecotic acid methyl ester;
L-Cysteinyl-4-(2,4-dichlorobenzyl)isonipecotic acid methyl ester;
L-Cysteinyl-4-(2,6-dichlorobenzyl)isonipecotic acid methyl ester;
L-Cysteinyl-4-(3-(2-methyl)pyridylmethyl)isonipecotic acid methyl ester;
L-Cysteinyl-4-(1-naphthyl)methyl isonipecotic acid methyl ester;
L-Cysteinyl-4-(1-naphthyl)methyl isonipecotic acid ethyl ester;
L-Cysteinyl-4-(1-naphthyl)methyl isonipecotic acid benzyl ester;
L-Cysteinyl-4-(2-methylbenzyl)isonipecotic acid 2-pyridylmethyl ester;
L-Cysteinyl-4-(2-methylbenzyl)isonipecotic acid 3-pyridylmethyl ester;
L-Cysteinyl-4-(2-methylbenzyl)isonipecotic acid 4-pyridylmethyl ester;
L-Cysteinyl-4-benzyl-4-piperidinol;
L-Cysteinyl-4-acetoxy-4-benzylpiperidine;
L-Cysteinyl-4-cyano-4-phenylpiperidine;
L-Cysteinyl-4-acetyl-4-phenylpiperidine;
L-Cysteinyl-4-methoxymethyl-4-(2-methylbenzyl)piperidine;
L-Cysteinyl-4-acetamido-4-(2-methylbenzyl)piperidine;
L-Cysteinyl-4-methylsulfonamido-4-(2-methylbenzyl)piperidine;
or the pharmaceutically acceptable salts.

3. A compound according to claim 2 that inhibits farnesyl-protein transferase which is:
L-Cysteinyl-4-(2-methylbenzyl)isonipecotyl N-methyl amide;
L-Cysteinyl-4-(2-methylbenzyl)isonipecotyl N-(2-pyridylmethyl) amide;
L-Cysteinyl-4-(2-methylbenzyl)isonipecotyl N-benzyl amide;
L-Cysteinyl-4-(2-methylbenzyl)isonipecotic acid methyl ester;
L-Cysteinyl-4-(2-chlorobenzyl)isonipecotic acid methyl ester;
L-Cysteinyl-4-(2,3-dichlorobenzyl)isonipecotic acid methyl ester;
L-Cysteinyl-4-(2,4-dichlorobenzyl)isonipecotic acid methyl ester;
L-Cysteinyl-4-(2,6-dichlorobenzyl)isonipecotic acid methyl ester;
L-Cysteinyl-4-(3-(2-methyl)pyridylmethyl)isonipecotic acid methyl ester;
L-Cysteinyl-4-(1-naphthyl)methyl isonipecotic acid methyl ester;
L-Cysteinyl-4-(1-naphthyl)methyl isonipecotic acid ethyl ester;
L-Cysteinyl-4-(1-naphthyl)methyl isonipecotic acid benzyl ester;
L-Cysteinyl-4-(2-methylbenzyl) isonipecotic acid 2-pyridylmethyl ester;
L-Cysteinyl-4-(2-methylbenzyl) isonipecotic acid 3-pyridylmethyl ester;
L-Cysteinyl-4-(2-methylbenzyl) isonipecotic acid 4-pyridylmethyl ester;
L-Cysteinyl-4-benzyl-4-piperidinol;
L-Cysteinyl-4-methoxymethyl-4-(2-methylbenzyl)piperidine;
or the pharmaceutically acceptable salts thereof.

4. The compound which is:
L-Cysteinyl-4-(2,3-dichlorobenzyl)isonipecotic acid methyl ester

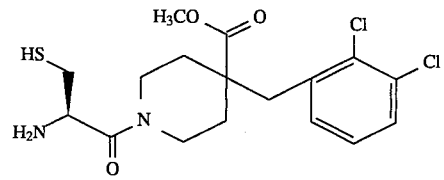

or a pharmaceutically acceptable salt thereof.

5. The compound which is:
L-Cysteinyl-4-(2,4-dichlorobenzyl)isonipecotic acid methyl ester

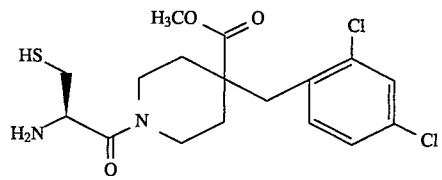

or a pharmaceutically acceptable salt thereof.

6. A pharmaceutical composition comprising a pharmaceutical carrier, and dispersed therein, a therapeutically effective amount of a compound of claim 1.

7. A pharmaceutical composition comprising a pharmaceutical carrier, and dispersed therein, a therapeutically effective amount of a compound of claim 2.

8. A method for inhibiting farnesyl-protein transferase which comprises administering to a mammal in need thereof a therapeutically effective amount of a composition of claim 6.

9. A method for inhibiting farnesyl-protein transferase which comprises administering to a mammal in need thereof a therapeutically effective amount of a composition of claim 7.

10. A method for treating cancer which comprises administering to a mammal in need thereof a therapeutically effective amount of a composition of claim 6.

11. A method for treating cancer which comprises administering to a mammal in need thereof a therapeutically effective amount of a composition of claim 7.

* * * * *